US006782289B1

(12) United States Patent
Strauss

(10) Patent No.: US 6,782,289 B1
(45) Date of Patent: Aug. 24, 2004

(54) METHODS AND APPARATUS FOR CHARACTERIZING LESIONS IN BLOOD VESSELS AND OTHER BODY LUMENS

(75) Inventor: H. William Strauss, Redwood City, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 221 days.

(21) Appl. No.: 09/670,412

(22) Filed: Sep. 26, 2000

Related U.S. Application Data

(60) Provisional application No. 60/159,001, filed on Oct. 8, 1999.

(51) Int. Cl.$^7$ ................................................. A61B 6/00
(52) U.S. Cl. ...................... 600/436; 600/431; 600/407
(58) Field of Search ............................... 600/431, 436, 600/407

(56) References Cited

U.S. PATENT DOCUMENTS

| | | | |
|---|---|---|---|
| 3,598,109 A | 8/1971 | Kobayashi | |
| 3,670,719 A | 6/1972 | Kobayashi et al. | |
| 4,444,744 A | * 4/1984 | Goldenberg | 424/1.1 |
| 4,647,445 A | 3/1987 | Lees | |
| 4,660,563 A | 4/1987 | Lees | |
| 4,877,599 A | 10/1989 | Lees | |
| 4,937,067 A | 6/1990 | Lees | |
| 5,088,492 A | 2/1992 | Takayama et al. | |
| 5,325,855 A | 7/1994 | Daghighian et al. | |

(List continued on next page.)

FOREIGN PATENT DOCUMENTS

| | | |
|---|---|---|
| EP | 0 788 766 | 8/1997 |
| WO | WO 89/10760 | 11/1989 |
| WO | WO 00/27278 | 5/2000 |
| WO | WO 01/64277 A2 | 3/2001 |

OTHER PUBLICATIONS

David R. Elmaleh et al. "Rapid noninvasive detection of experiment atherosclerotic lesions with novel $^{99m}$Tc–labeled diadenosine tetraphosphates" *Proc. Natl. Acad. Sci. USA*, vol. 95, pp. 691–695, Jan. 1998 Medical Sciences.

Shankar Vallabhajosula and Valentin Fuster, "Atherosclerosis: Imaging Techniques and the Evolving Role of Nuclear Medicine", *The Journal of Nuclear Medicine*, vol. 38, No. 11, Nov. 1997.

Sasha M. Demos, et al. "In Vitro Targeting of Antibody–Conjugated Echogenic Liposomes for Site–Specific Ultrasonic Image Enhancement" *Journal of Pharmaceutical Sciences*, vol. 86, No. 2, Feb. 1997.

Jagat Narula, et al. "Noninvasive Localization of Experimental Atherosclerotic Lesions With Mouse/Human Chimeric Z2D3 F (ab')$_2$ Specific for the Proliferating Smooth Muscle Cells of Human Atheroma" 1995 *American Heart Association, Inc.*, Circulation, vol. 92, No. 3, Aug. 1, 1995.

(List continued on next page.)

*Primary Examiner*—Willis R. Wolfe
*Assistant Examiner*—Johnny H. Hoang
(74) *Attorney, Agent, or Firm*—Bret E. Field; Bozicevic, Field & Francis LLP

(57) ABSTRACT

Methods, devices, and kits, for assessing luminal lesions are provided. The subject devices comprise an intraluminal detector capable of sensing radioactive or other labels. In the subject methods, a detectable marker is introduced to a body lumen, either into the lumen itself or systemically in patient circulation, and localizes at a lesion. The detector is introduced into the body lumen and the distribution of a localized marker detected in situ. The information is useful for a number of purposes including the identification of unstable plaque in patients suffering from atherosclerotic disease.

37 Claims, 1 Drawing Sheet

U.S. PATENT DOCUMENTS

Figure 1:
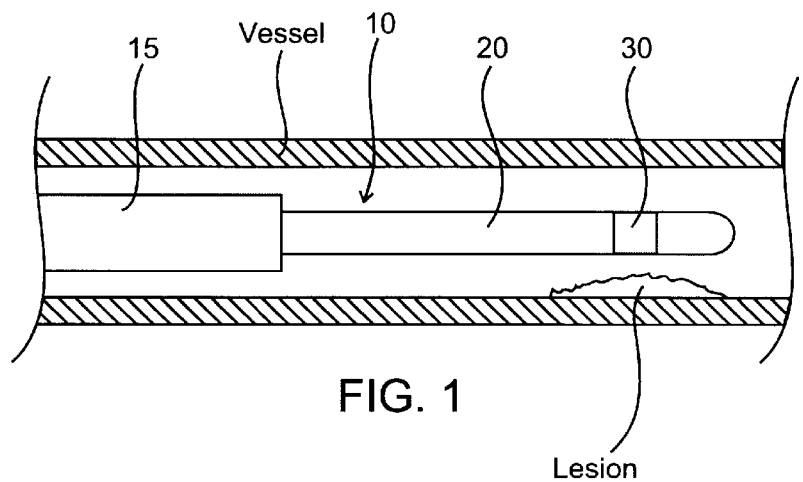

| | | | |
|---|---|---|---|
| 5,395,319 A | * | 3/1995 | Hirsch et al. .................. 604/60 |
| 5,423,334 A | * | 6/1995 | Jordan ........................ 128/899 |
| 5,424,546 A | | 6/1995 | Okada et al. |
| 5,429,133 A | | 7/1995 | Thurston et al. |
| 5,449,921 A | | 9/1995 | Baba |
| 5,510,466 A | | 4/1996 | Krieger et al. |
| 5,711,931 A | | 1/1998 | Dean et al. |
| 5,716,595 A | | 2/1998 | Goldenberg |
| 5,726,153 A | | 3/1998 | Lees et al. |
| 5,751,781 A | | 5/1998 | Brown et al. |
| 5,811,814 A | | 9/1998 | Leone et al. |
| 5,833,603 A | * | 11/1998 | Kovacs et al. ............... 600/317 |
| 5,871,449 A | | 2/1999 | Brown |
| 5,906,636 A | | 5/1999 | Casscells, III et al. |
| 5,924,997 A | | 7/1999 | Campbell |
| 5,932,879 A | | 8/1999 | Raylman et al. |
| 5,935,075 A | | 8/1999 | Casscells et al. |
| 6,031,892 A | | 2/2000 | Karellas |
| 6,113,593 A | | 9/2000 | Tu et al. |
| 6,161,034 A | * | 12/2000 | Burbank et al. ............. 600/431 |
| 6,173,715 B1 | * | 1/2001 | Sinanan et al. ............. 128/899 |
| 6,254,548 B1 | * | 7/2001 | Ishikawa et al. ............ 600/549 |
| 6,356,782 B1 | * | 3/2002 | Sirimane et al. ............ 600/431 |
| 6,363,940 B1 | * | 4/2002 | Krag .......................... 128/899 |

OTHER PUBLICATIONS

Ann M Lees, et al. "Imaging Human Atherosclerosis with $^{99m}$Tc–labeled Low Density Lipoproteins" *Arteriosclerosis*, vol. 8, No. 5, Sep./Oct. 1988.

Ohdaira et al. (1999) "Intraoperative Localization of Colorectal Tumors in the Early Stages Using a Marking Clip Detector System." *Diseases of the colon and rectum*, vol. 42(10):1353–5.

Parsons (1996) "Fluoroscopically assisted thromboembolectomy: An improved method for treating acute arterial occlusions." *Annals of Vascular Surgery*, vol. 10(3):201–10.

\* cited by examiner

METHODS AND APPARATUS FOR CHARACTERIZING LESIONS IN BLOOD VESSELS AND OTHER BODY LUMENS

This application claims the benifit of Provisional Application Ser. No. 60/159,001 Filed Oct. 8, 1999.

BACKGROUND OF THE INVENTION

1. Field of the Invention

The present invention relates generally to medical devices and methods. More particularly, the present invention relates to devices and methods for the intraluminal characterization of lesions in blood vessels and other body lumens.

Coronary artery disease resulting from the build-up of atherosclerotic plaque in the coronary arteries is a leading cause of death in the United States and worldwide. The plaque build-up causes a narrowing of the artery, commonly referred to as a lesion, which reduces blood flow to the myocardium (heart muscle tissue). Myocardial infarction (better known as a heart attack) can occur when an arterial lesion abruptly closes the vessel, causing complete cessation of blood flow to portions of the myocardium. Even if abrupt closure does not occur, blood flow may decrease resulting in chronically insufficient blood flow which can cause significant tissue damage over time.

A variety of interventions have been proposed to treat coronary artery disease. For disseminated disease, the most effective treatment is usually coronary artery bypass grafting where problematic lesions in the coronary arteries are bypassed using external grafts. In cases of less severe disease, pharmaceutical treatment is often sufficient. Finally, focused disease can often be treated intravascularly using a variety of catheter-based approaches, such as balloon angioplasty, atherectomy, radiation treatment, stenting, and often combinations of these approaches.

With the variety of treatment techniques which are available, the cardiologist is faced with a challenge of selecting the particular treatment which is best suited for an individual patient. While numerous of diagnostic aids have been developed, no one technique provides all the information which is needed to select a treatment. Angiography is very effective in locating lesions in the coronary vasculature, but provides little information concerning the nature of the lesion. To provide better characterization of the lesion(s), a variety of imaging techniques have been developed for providing a more detailed view of the lesion, including intravascular ultrasound (IVUS), angioscopy, laser spectroscopy, computed tomography (CT), magnetic resonance imaging (MRI), and the like. None of these techniques, however, is completely successful in determining the exact nature of the lesion. In particular, such techniques provide little information regarding whether the plaque is stable or unstable.

Plaques which form in the coronaries and other vessels comprise inflammatory cells, smooth muscles cells, cholesterol, and fatty substances, and these materials are usually trapped between the endothelium of the vessel and the underlying smooth muscle cells. Depending on various factors, including thickness, composition, and size of the deposited materials, the plaques can be characterized as stable or unstable. The plaque is normally covered by a cap and/or an endothelial layer. When the cap and/or endothelial layer is disrupted, the ruptured plaque releases highly thrombogenic constituent materials which are capable of activating the clotting cascade and inducing rapid and substantial coronary thrombosis. Such plaque is referred to as unstable or "vulnerable," and the resulting thrombus formation can cause unstable angina chest pain, acute myocardial infarction (heart attack), sudden coronary death, and stroke. It has recently been proposed that plaque instability, rather than the degree of plaque build-up, should be the primary determining factor for treatment selection.

A variety of approaches for distinguishing stable and unstable plaque in patients have been proposed. Some of the proposals involve detecting a slightly elevated temperature within unstable plaque resulting from inflammation. Other techniques involve exposure of the plaque to infrared light. It has also been proposed to introduce radiolabeled materials which have been shown by autoradiography to bind to stable and unstable plaque in different ways. External detection of the radiolabels, however, greatly limits the sensitivity of these techniques and makes it difficult to determine the precise locations of the affected regions. Thus far, none of these technologies has possessed sufficient sensitivity or resolution necessary to reliably characterize the plaque at the cellular level in the intact animal or man.

For all of these reasons, it would be desirable to provide improved methods and apparatus for distinguishing between stable and unstable plaque within the coronary and other patient vasculature. It would be further desirable if such methods and techniques could be applied to characterizing lesions in other body lumens, which are associated with other disease conditions. The methods and devices of the present invention should preferably be able to be implemented in situ, i.e., within the body lumen being assessed, and should preferably be able to interrogate the body lumen over a relatively long distance to characterize disseminated disease in an efficient fashion. The methods and devices should provide highly sensitive detection so that even minor differences between regions of plaque or other lesions can be determined, and should permit assessment in real time, preferably without the need for prolonged placement of the devices within a patient. At least some of these objectives will be met by the inventions described hereinafter.

2. Description of the Background Art

The use of radiolabeled agents for detecting atherosclerotic lesions is described in the medical literature. See, for example, Elmaleh et al. (1998) *Proc. Natl. Acad. Sci. USA* 95:691–695; Vallabhajosula and Fuster (1997) *J Nucl. Med.* 38:1788–1796); Demos et al. (1997) *J Pharm. Sci.* 86:167–171; Narula et al. (1995) *Circulation* 92: 474–484; and Lees et al. (1998) *Arteriosclerosis* 8:461–470. U.S. Pat. No. 4,660,563, describes the injection of radiolabeled lipoproteins into a patient where the lipoproteins are taken up into regions of arteriosclerotic lesions to permit early detection of those lesions using an external scintillation counter. U.S. Pat. No. 5,811,814, describes and intravascular radiation-detecting catheter. The catheter is used to locate tagged red blood cells that may accumulate, for example, in an aneurysm. U.S. Pat. No. 5,429,133, describes a laparoscopic probe for detecting radiation concentrated in solid tissue tumors. Miniature and flexible radiation detectors intended for medical use are produced by Intra-Medical LLC, Santa Monica, Calif. (www.intra-medical.com). See also U.S. Pat. Nos. 4,647,445; 4,877,599; 4,937,067; 5,510, 466; 5,711,931; 5,726,153; and WO 89/10760.

SUMMARY OF THE INVENTION

Methods, systems, and kits, are provided for assessing characteristics of lesions and other target sites within body lumens, particularly atherosclerotic lesions within a patient's vasculature, including the coronary vasculature, peripheral vasculature, and cerebral vasculature. The present invention relies on introducing a labeled marker, typically a radiolabeled marker, to the patient in such a way that the marker localizes within the lesion or target site in some manner which enables or facilitates assessment of that target site. Introduction of the labeled marker can be systemic, e.g., by injection or infusion to the patient's blood circulation for evaluation of lesions in the vasculature or other body lumens. Alternatively, introduction of the labeled markers can be local, e.g., by catheter delivery directly to a target site within a blood vessel or other body lumen. Moreover, the labeled marker could be introduced systemically and locally in various combinations. After introduction to the patient, the labeled marker is taken up by the lesion or other target site, and the amount of marker (accumulation), rate of uptake, distribution of marker, or other marker characteristics then determined in order to facilitate or enable diagnosis or other evaluation of the lesion. In particular, according to the present invention, the amount, rate of uptake, and/or distribution of the marker at or near the lesion or other target site is measured in situ using a detector which has been introduced into the body lumen and positioned in a known or measurable relationship to the lesion or other target site.

DETAILED DESCRIPTION OF THE DRAWINGS

Figure 2:
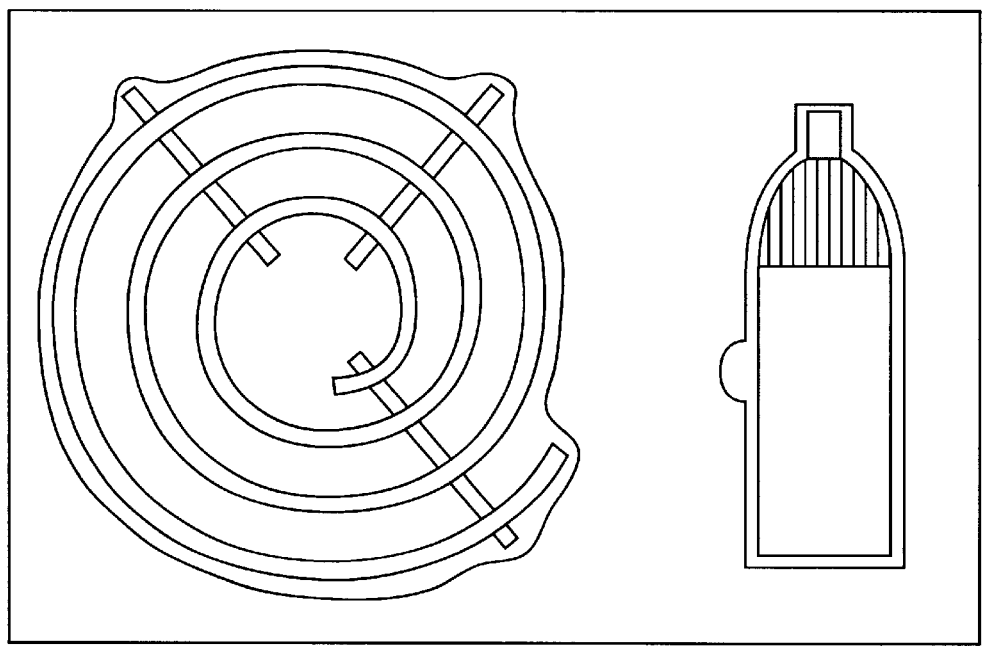

FIG 1. is a cross-sectional view of a vessel illustration the present invention disposed therein; and FIG 2. is an exemplary embodiment of a kit in accordance with the present invention.

DETAILED DESCRIPTION OF PREFERRED EMBODIMENTS

While the present invention will find particular use in the diagnosis of diseased lesions within the vasculature, most particularly in the diagnosis of coronary artery disease in the coronary vasculature, it will also be useful in a wide variety of other circumstances where uptake of a labeled substance can be related to diagnosis of a disease or other evaluation of a body lumen. For example, by introducing labeled cellular precursor materials, such as labeled amino acids, labeled nucleotides and nucleosides, or the like, various conditions related to excessive cellular proliferation can be assessed and monitored. For example, the presence or prognosis of various luminal cancers can be determined, such as cancer of the urinary bladder, colon cancer, esophageal cancer, prostate cancer (as well as benign prostate hyperplasia), lung cancer and other bronchial lesions, and the like, can be made.

The detection of the labeled marker in situ within a body lumen has a number of significant advantages. Such in situ detection allows the detection of labels, such as visible light, fluorescence, luminescence, and the like, which cannot be detected externally. With tissue-penetrating labels, such as radioisotopic radiation, in situ detection is much more sensitive than external detection. This is particularly the case when lower energy (short-path length) radiation sources are used, such as beta ($\beta$) radiation, conversion electrons, and the like. Detection of lower energy radiation reduces the background which is observed when the tracer concentrates in an adjacent organ or tissue, and is usually not feasible with external detection which, for example, relies on the introduction of gamma ($\gamma$) radiation-emitting labels and the use of gamma ($\gamma$) cameras. The present invention, however, is not limited to the use of beta ($\beta$) radiation, conversion electrons, and other short path length radiation, but instead may find use with all types of ionizing radiation under appropriate circumstances.

In situ detection also improves detection of both the position and distribution of label immobilized within the body lumen. It will be appreciated that the detectors can be configured and/or repositioned so that immobilized radiation and other labels can be determined with an accuracy of less than 5 mm, usually less than 3 mm, preferably less than 2 mm, and often less than 1 mm, along the axis of the body lumen. The ability to accurately locate a target site, such as a region of unstable plaque, a region of proliferating cells, or the like, can greatly facilitate subsequent treatment.

The labeled marker will usually comprise at least two components, i.e., a detectable label and a binding substance. The detectable label can be any natural or synthetic material which is capable of in situ detection using an intravascular catheter or other intraluminal detector. Particularly suitable are radiolabels comprising radionuclides which emit beta ($\beta$) radiation, conversion electrons, and/or gamma ($\gamma$) radiation. Presently preferred are radiolabels which emit primarily beta ($\beta$) radiation or conversion electrons which have a relatively short path length and permit more precise localization of the target site or material. In certain embodiments, it may be desirable to use both beta and gamma radiation emitting markers or radiolabels. In such embodiments, by using detector(s) capable of quantifying both beta ($\beta$) and gamma ($\gamma$) radiation, it will be possible to gauge how close the detector is to the label based on the observed ratio of beta ($\beta$)/gamma ($\gamma$) radiation and the known emission characteristics of the label. That is, the relative decline in observed beta ($\beta$) radiation will indicate that the detector is further from the label.

In addition to radiolabels, the present invention can employ other visible markers including fluorescent labels, such as fluorescein, Texas Red, phycocyanin dyes, arylsulfonate cyanine dyes, and the like; chemiluminescent labels, and/or bioluminescent labels. The present invention can also employ passive labels which respond to interrogation in various ways. For example, the labels may comprise paramagnetic or superparamagnetic materials which are detected based on magnetic resonance. Alternatively, the labels may be acoustically reflective or absorptive, allowing detection by ultrasonic reflection. Further, the labels could be absorptive or reflective to infrared radiation, allowing detection by optical coherence tomography. Still further, the labels may be activated or fluoresce in the pesence of an appropriate exciting source of energy.

The labels will typically be bound, covalently or noncovalently, to the binding substance. The binding substance can be virtually any material which becomes incorporated into and/or bound to a desired intraluminal target site. Thus, in the case of intravascular detection and labeling of atherosclerotic lesions, the material may be a natural substance which becomes incorporated into the lesions, such as low-density lipoproteins or components thereof. In the case of excessive self-proliferation, the binding substances can be a variety of cellular precursors, including proteins, nucleic acids, and the like. In addition to natural materials which become incorporated into a growing or proliferating target site, the binding substances can be prepared or synthesized for specific binding to a target site at the target location. For example, antibodies can be prepared to a wide variety of vascular and non-vascular target sites. Additionally, in some cases, natural receptors and/or ligands will be available for particular target sites. For example, monocyte chemoattractant peptide 1 (MCP1) localizes on receptors upregulated by the macrophages in plaque. Other target substance in plaque include lectins whose receptors are upregulated on endothelial cells that overly the plaque. Antibodies such as Z2D3

(Khaw et al., Carrio et al., Narula et al.) localize on proliferating smooth muscle in the plaque. Another potential agent is fluorodeoxyglucose labeled with fluorine-18. This agent emits positrons and is utilized as an energy substrate by macrophages and monocytes, and it has shown enhanced localization in experimental atherosclerosis models. Still further, agents include those which bind to tissue factor, lymphocyte surface antigens or secreted compounds, and other secreted proteins that become entrapped within and characteristics of vulnerable plaque.

The label and binding substance may be bound to each other in any conventional manner. Most commonly, moieties on the label and/or the binding substance will be derivitized to permit covalent attachment. Covalent attachment will usually be direct, but in some cases may employ a linking member. Non-covalent attachment can employ a variety of non-covalent linkers, such as biotin, avidin, intermediate antibodies, receptors, ligands, and the like. A variety of suitable binding techniques are described in a review article in Nature Biotechnology (1999) Vol. 17, pages 849 and 850, the full disclosure of which is incorporated by reference.

A variety of suitable labeled markers have been proposed in the medical and scientific literature. See, for example, U.S. Pat. Nos. 4,647,445; 4,660,563; 4,937,067; 4,877,599; 5,510,466; 5,711,931; 5,726,153; and WO 89/10760. Each of these patent references is hereby incorporated in its entirety by reference.

An important aspect of the present invention is the ability to detect and/or image the label in situ after the label has localized in the blood vessel wall or other body lumen. Because the label binds to specific target materials within the body lumen, the pattern in which the label has localized will correspond to the pattern of the target material in the body lumen. Such separate detection may be performed simultaneously, sequentially, or in some combination thereof. For example, if the labeled marker comprises low-density lipoproteins, or a component thereof, the labeled marker will bind to atherosclerotic plaque which is actively growing or accumulating and therefore at risk of being unstable. The pattern of label will thus correspond to the pattern of unstable plaque within the patient's vasculature.

Detection of the label and its pattern within the body lumen will be performed using an intraluminal detector, usually a detector capable of detecting ionizing radiation from a radioisotopic label within a particular distance of the label, as discussed in more detail below. The detector and catheter can be introduced into the body lumen by a variety of conventional techniques. For intravascular detectors the preferred techniques will be percutaneous, e.g., using a needle and sheath for introduction of a guidewire in a Seldinger access technique. Alternatively, surgical cutdowns can be used for accessing blood vessels, and a variety of other surgical and minimally invasive techniques can be used for introducing intraluminal detectors into other body lumens.

The nature of the label and characteristics of the detector will be selected so that an emitted signal from the label will be visible or detectable only within a particular distance of a detecting surface or element of the detector, usually within 5 mm, preferably within 3 mm, and sometimes within 1 mm. That is, the detector will only have a limited range for viewing localized label so that background from label located remotely from the detector will not be detected. In this way, accurate positional detection of the label can be achieved. In a presently preferred embodiment, the label will emit beta ($\beta$) radiation or conversion electrons or low energy x-rays which have a very short path length. The sensitivity of the detector will then be selected so that the beta ($\beta$) radiation will be visible only over a very short distance, typically less than 3 mm, preferably less than 1 mm. Moreover, the detector may be configured so that its detector surface(s) or element(s) will be engaged directly against the wall of the blood vessel or other body lumen to enhance detection of the charged particle radiation.

In a particular aspect of the present invention, detection of the label will be performed over a minimum length of the body lumen in order to characterize variations in the luminal lesion over that length with the ability to distinguish lesions present at intervals of 3 mm. For example, in blood vessels, the present invention will usually be used to image over a vascular length of at least 30 mm, preferably at least 40 mm, and more preferably at least 50 mm. Such detection may be achieved by scanning a detector over the length within the blood vessel or other body lumen. Preferably, however, the detector can remain stationary within the lumen and have spatial resolution over the preferred minimum length set forth above without movement of the detector itself.

In addition to the minimum detection lengths set forth above, the detectors will preferably be isotropic over at least their circumference or periphery. Regardless of whether the detector is scanned or held stationary during detection, it will normally be preferred that detection of label over the entire circumference or periphery of the body lumen be performed. In other cases, however, it might be desired to perform a directional scan i.e., one where a particular radial sector of the body lumen wall is observed.

In some cases, it may be preferred to employ two or more labels and to separately detect those labels in order to determine the spacial distribution of more than one material in the body lumen. For example, plaques at different phases of development have varying degrees of smooth muscle proliferation (detectable with Z2D3 antibody localization), varying degrees of macrophage infiltration (detectable with MCP1), varying levels of macrophage metabolism (detectable with the metabolic substrate FDG), and varying degrees of metalloproteinase activity (detectable with labeled antibodies specific for the metalloproteinase). Two or more parameters could be evaluated simultaneously if the radiopharmaceuticals carry radiolabels with substantially different energies or if one radionuclide has a substantially shorter half life than the other(s). Alternatively, labels having different natures, e.g., light emission, fluorescence emission, and/or radioisotopic radiation could be employed and detected simultaneous with minimum interference.

Detection of the localized marker can provide useful information regarding a lesion or other structural condition of the body lumen. As described above, the present invention will permit determination of the axial and circumferential distribution of the target material within the body lumen. In the case of atherosclerotic lesions in a blood vessel, this information is particularly suitable for assessing the need for treatment as well as planning particular treatment modalities. In particular, the present invention would allow the identification of relatively small lesions, e.g., with luminal blockage below 50%, which nonetheless are unstable and require immediate intervention. Conversely, larger lesions (above 50% occlusion) which are stable and less in need of immediate intervention can also be identified.

While the present invention is directed at intraluminal detection of marker(s), it may find use in combination with external detection of the same or other markers and/or external detection and imaging of the catheter which is being used for the intraluminal detection. External detection of immobilized markers may be useful for prepositioning of the intraluminal detection catheter and/or for comparing information from different markers and targets (where the different markers may be bound to different binding substances having different specificities). External detection of the catheter will allow mapping of the vasculature or other luminal system. The position of the catheter can be detected fluoroscopically, by MRI, or otherwise, and the position of the internally detected lesions be noted on the external image or map which is created.

As shown in FIG. 1, the present invention further provides radiation detection devices 10 comprising an elongated body 20, and a radiation detector 30 disposed on the elongated body 20. The catheter or other elongate body 20 is configured to access the interior of a target body lumen, such as a blood vessel, a ureter, a urethera, an esophagus, a cervix, a uterus, a bladder, or the like. The radiation detector 30 is capable of sensing radiation emitted into the body lumen and which is incident along the elongate body. In a first particular embodiment, the radiation detector will be capable of sensing radiation over a length of at least 3 cm, preferably at least 4 cm, and more preferably at least 5 cm. Optionally, the radiation detector will be capable of sensing radiation isotropically preferably being equally sensitive in all radial directions over the circumference of the elongated body 20.

In a second specific embodiment, the radiation detectors of the present invention will be capable of distinguishing radiation from at least two different radioactive labels with energies that differ by a threshold level.

In a third specific embodiment, the radiation detectors 10 of the present invention will be capable of being axially translated within the body to sense radiation incident along the body over a length of at least 3 cm, preferably at least 4 cm, and more preferably at least 5 cm. Usually, such devices will comprise a catheter having an outside body 15 which can remain stationary within a blood vessel and an internal detector 10 which can be axially translated within the stationary body 15. Alternatively, the entire catheter may be translated within the lumen to cover the desired length.

Optionally, the catheters may comprise two or more different detection systems. Thus, in addition to the label detection system, the catheters might further indicate optical, ultrasonic, OCT, MR or other imaging systems. This will allow image information from the catheter to be "registered" or coordinated with the lesion characteristics also detected by the catheter. In some instances, it might be useful to provide for catheter-based excitation of a first or second label which has been immobilized at a target site.

The present invention still further comprises kits for identifying or assessing luminal lesions or other target sites. The kits will comprise a radiation detector configured to be introduced into a body lumen and instructions for use according to any of the methods described above.

Alternatively, as shown in FIG. 2, kits 100 according to the present invention may comprise a radiation detector 10 configured to be introduced into a body lumen, a container 105 for holding a reagent comprising a substance capable of binding to a target material within the body lumen and a detectable label bound to the substance, and a package 115 for holding the radiation detector and the container together. The container may be any conventional container, such as a box, tray, tube, pouch, or the like. Instructions for use will typically be provided on a separate package insert, but in some cases may be printed in whole or in part on the packaging itself. Usually, the radiation detector will be maintained sterilely within the packaging.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for identifying or assessing a luminal lesion, said method comprising:
   introducing a first detectable marker into a body lumen, wherein said first detectable marker localizes at a lesion comprising a material which preferentially binds or incorporates the first detectable marker;
   introducing a detector into the body lumen; and
   detecting the first detectable marker localized at said lesion using the detector.

2. A method as in claim 1, wherein introducing said first detectable marker comprises introducing a radioactive marker.

3. A method as in claim 2, wherein introducing the radioactive marker comprises introducing a radioisotope which emits beta ($\beta$) radiation.

4. A method as in claim 1, wherein introducing the detectable marker comprises systemic introduction of the marker.

5. A method as in claim 1, wherein introducing the detectable marker comprises local introduction through the detector.

6. A method as in claim 1, wherein introducing the first detectable marker comprises systemic injection into a patient's vasculature.

7. A method as in claim 1, wherein introducing the detector comprises percutaneous introduction of a catheter into the body lumen, wherein the catheter comprises the detector.

8. A method as in claim 1, wherein introducing the detector comprises surgically accessing the body lumen to create an access passage and advancing the catheter through the passage into the body lumen, wherein the catheter comprises the detector.

9. A method as in claim 1, wherein detecting the first detectable marker localized at said lesion, comprises detecting the first detectable marker within 5 cm of a detection surface of the detector.

10. A method as in claim 1, wherein the marker emits beta ($\beta$) radiation and the detector detects beta ($\beta$) radiation.

11. A method as in claim 1, wherein detecting the first detectable localized marker comprises scanning a segment of the lesion having a length of at least 3 cm.

12. A method as in claim 11, wherein detecting the first detectable localized marker comprises scanning a segment of the lesion having a length of at least 4 cm.

13. A method as in claim 11, wherein scanning the segment comprises positioning said detector having a detection surface and scanning while the detector remains stationary in the body lumen.

14. A method as in claim 11, wherein scanning the segment comprises positioning said detector and repositioning the detector to scan the entire segment.

15. A method as in any of claim 1, wherein detecting the localized marker comprises isotropically detecting marker disposed about a periphery of the body lumen.

16. A method as in claim 1, further comprising:
   introducing a second detectable marker to the body lumen, wherein said second detectable marker localizes at a lesion comprising a second material which preferentially binds the second detectable marker; and
   detecting the second detecting marker.

17. A method as in claim 16, wherein the second detectable marker is detected using the same detector as detected the first detectable marker.

18. A method as in claim 16, wherein the second detectable marker is detected using a second detector.

19. A method as in claim 1, wherein the body lumen is selected from a blood vessel, a ureter, a urethra, an esophagus, a cervix, a uterus or a bladder.

20. A method as in claim 1, wherein said first detectable marker is a fluorescent marker.

21. A method for assessing stability of an intravascular lesion, said method comprising:

introducing a radiolabeled substance into a blood vessel, wherein the radiolabeled substance is selectively incorporated into plaque which is at increased risk of rupture;

introducing a detector into the blood vessel; and determining to which degree the radiolabeled substance has been incorporated into a lesion, whereby an assessment of lesion stability may be made.

22. A method as in claim 21, wherein introducing the radiolabeled substance comprises introducing a radioisotope which emits beta ($\beta$) radiation.

23. A method as in claim 21, wherein introducing radiolabeled substance comprises systemic introduction of the marker.

24. A method as in claim 21, wherein introducing the radiolabeled substance comprises local introduction through the detector.

25. A method as in claim 21, wherein introducing the radiolabeled substance comprises systemic injection into a patient's vasculature.

26. A method as in claim 21, wherein introducing the detector comprises percutaneous introduction of a catheter into the blood vessel, wherein the catheter comprises the detector.

27. A method as in claim 21, wherein introducing the detector comprises surgically accessing the blood vessel to create an access passage and advancing the catheter through the passage into the blood vessel, wherein the catheter comprises the detector.

28. A method as in claim 21, wherein determining the degree of incorporation comprises detecting radiolabeled substance within 5 cm of a detection surface of the detector.

29. A method as in claim 28, wherein the radiolabeled substance emits beta ($\beta$) radiation and the detector detects beta ($\beta$) radiation.

30. A method as in claim 21, wherein determining the degree of incorporation comprises scanning a segment of the lesion having a length of at least 3 cm.

31. A method as in claim 30, wherein determining the degree of incorporation comprises scanning a segment of the lesion having a length of at least 4 cm.

32. A method as in claim 30, wherein scanning the segment comprises positioning the detector having a detection surface and scanning while the detector remains stationary in the body lumen.

33. A method as in claim 30, wherein scanning the segment comprises positioning the detector and repositioning the detector to scan the entire segment.

34. A method as in claim 21, wherein determining the degree of incorporation comprises isotropically detecting marker disposed about a periphery of the body lumen.

35. A method as in claim 21, further comprising:

introducing a second radiolabeled substance to the blood vessel, wherein said second radiolabeled substance localizes at a lesion comprising a second material which preferentially binds the lesion; and detecting the second radiolabeled substance.

36. A method as in claim 35, wherein the second radiolabeled substance is detected using the same detector as detected the first radiolabeled substance.

37. A method as in claim 35, wherein the second radiolabeled substance is detected using a second detector.

\* \* \* \* \*